United States Patent [19]

Aston

[11] Patent Number: 5,506,204
[45] Date of Patent: Apr. 9, 1996

[54] MURAMYL COMPOUNDS FOR TREATMENT OF SEPTIC SHOCK

[75] Inventor: Roger Aston, Malmesbury, United Kingdom

[73] Assignee: Peptech (UK) Limited, England

[21] Appl. No.: 244,154

[22] PCT Filed: Nov. 19, 1992

[86] PCT No.: PCT/GB92/02137

§ 371 Date: May 18, 1994

§ 102(e) Date: May 18, 1994

[87] PCT Pub. No.: WO93/10148

PCT Pub. Date: May 27, 1993

[30] Foreign Application Priority Data

Nov. 19, 1991 [GB] United Kingdom ............... 9124500
May 8, 1992 [GB] United Kingdom ............... 9210013

[51] Int. Cl.[6] .................... A61K 38/16; C07K 9/00
[52] U.S. Cl. .................................... 514/8; 530/322
[58] Field of Search ........................ 514/8; 530/322

[56] References Cited

U.S. PATENT DOCUMENTS 4,382,080 5/1983 Shiba et al. .
4,395,399 6/1983 Ovchinnikov et al. ............ 424/177

FOREIGN PATENT DOCUMENTS 0015810 9/1980 European Pat. Off. .
0331756 9/1989 European Pat. Off. .

OTHER PUBLICATIONS

Parant, M. et al., *Journal of Leukocyte Biology* 47:164–169 (1990).
Parant, M. and Chedid, L., *Adv. Exp. Med. Biol.* 256:537–547 (1990).
Kodama, M. et al. *Chemical Abstracts* 110:234 (1989).
Matsumoto, K. et al., *Chemical Abstracts* 96:441 (1982).
Cheadle, W. G. et al., *The American Surgeon* 52:613–617 (1986).
Matsumoto, K. et al., *Infection and Immunity* 32:748–758 (1981).
Cadby, P. A. et al., *In Progress in the Chemistry of Organic Natural Products–40*, Published by Springer–Verlag, Wien, Austria, pp. 9–13 (1981).
Kobayashi, S. et al., *Bull. Chem. Soc. Japan* 53:2570–2577 (1980).
Emmett, J. C. in *Comprehensive Medicinal Chemistry* 3:1118–1120 (1990) Pergamon Press.
Werner, G. H. et al., *Experientia* 42:521–531 (1986).
Lederer, E., *Journal of Medicinal Chemistry* 23:819–825 (1980).
Izbicki, J. R. et al., *Infection and Immunity* 59:126–130 (1991).

Primary Examiner—Christina Y. Chan
Assistant Examiner—Benet Prickril
Attorney, Agent, or Firm—Banner & Allegretti, Ltd.

[57] ABSTRACT

Muramyl peptide compounds which: (a) are non-pyrogenic; and/or (b) ameliorate endotoxin-induced weight loss and/or hypophagia; and/or (c) reduce TNF production; and/or (d) stimulate macrophage to produce endotoxin are useful, in the treatment of septic shock, cachexia and other life-threatening inflammatory conditions. Preferred compounds include N-acetyl-glucosaminyl-N-acetyl-muramyl-L-alanyl-D-isoglutamine (GMDP) and N-acetyl-glucosaminyl-N-acetyl-muramyl-L-alanyl-D-glutamic acid (GMDP-A).

8 Claims, 4 Drawing Sheets

MURAMYL COMPOUNDS FOR TREATMENT OF SEPTIC SHOCK

This invention relates to the treatment and prophylaxis of sepsis, septic shock and other life-threatening inflammatory conditions.

The mortality of systemic bacterial infection (bacteraemia) is high, particularly for gram-negative infections, where mortality levels are still comparable to those of several decades ago. Hospital-acquired infections have a higher mortality than community-acquired infections; post-operative complications due to bacterial infections represent a real problem in many hospitals of the world. The mortality of gram-negative bacteraemia is frequently due to septic shock.

Septic shock (also known as toxic shock) is an acute life-threatening inflammatory condition characterised by hypotension and/or evidence of organ hypoperfusion. The hypotension results from reduced vascular resistance. Multiple organ failure and abnormalities of coagulation frequently develop.

Current management of septic shock includes intensive haemodynamic monitoring with aggressive fluid replacement if necessary to correct hypovolaemia, and the administration of inotropes to raise the blood pressure by increasing the cardiac output. Some of these drugs, particularly noradrenaline, also cause vasoconstriction, and so increase peripheral resistance. Additional supported measures are frequently required, including haemodialysis, mechanical ventilation and parenteral nutrition. The underlying infection is treated with anti-infective agents such as antibiotics or other antibacterials.

Other life-threatening inflammatory conditions include cachexia, which is a chronic condition which may arise from cancer or chronic infections, for example by viruses such as the HIV virus. Cachexia is characterised by abnormal lipid metabolism with hypertriglyceridaemia, abnormal protein and glucose metabolism and body wasting. It may also be implicated in systemic bacterial infections.

The invention also relates to other infections and inflammatory conditions such as pneumonia, surgical wound infection, suppuration of the small pelvis, peritonitis, peritoneal abscess, paracolostomic abscess, cholangitis, empyema of the gall bladder, phlegmon of front abdomen, phlegmon of the sigma and postinjective abscess, as well as to the related complications of endotoxaemia, glucose depression, hypotension, cardiac arrythmia and vasodilation.

There are today many impressive anti-infective agents available to the medical practitioner. Antibiotics form an important sub-group of antibacterials. Antibiotics are anti-bacterial agents derived from microorganisms; they include the penicillins, streptomycin, chloramphenicol and chlortetracycline. The discovery and isolation of the penicillin nucleus, 6-amino-penicillanic acid (6-APA) in 1958 provided the basis for the synthesis of a large number of new penicillins, many of which are still in use. Other antibacterials apart from antibiotics also form the basis of many treatment regimes: examples include the sulphonamides and trimethoprim, which are often co-administered.

Because of the continued increase and high incidence of life-threatening inflammatory conditions such as septic shock, it is apparent that the availability of a large number of chemotherapeutic agents including effective anti-bacterial drugs has not solved the problem of treating and preventing them. In fact, effective anti-bacterial chemotherapy may paradoxically increase the likelihood of septic shock and other complications: endotoxin or its constituent lipopolysaccharide fragments from the walls of killed bacterial cells may be mediators for septic shock, possibly by leading to enhanced levels of tumour necrosis factor (TNF), particularly TNFα. It is to the problem of treating or preventing septic shock and other life-threatening inflammatory conditions that the present invention is addressed.

It has been discovered that a group of muramyl peptide compounds is useful in treating or preventing progressive septicaemia and septic shock. Certain muramyl dipeptides (MDPs) have previously been disclosed as having immunopotentiating, anti-tumour and certain anti-bacterial activities. However, MDPs have been shown to synergise the activity of endotoxin (Parant, M. and Chedid, L. "Various Aspects of Synergism between Endotoxin and MDPs", *Adv. Exptl. Med. Biol.* 256 537–547 (1990)) or at least to exacerbate its effect (Langhans et al, *Am. J. Physiol.* 261 R659 (1991)) and so would hardly be expected to be useful in treating conditions believed to be mediated, at least in part, by endotoxin. Further, the fact that the pharmaceutical utility which forms the basis of the present invention cannot be predicted from the known antibacterial action of MDPs is evidenced by the large number of known antibacterials which fail to meet the clinician's needs in combatting septic shock and other frequently fatal inflammatory conditions.

The present invention is based on the discovery that, in spite of the fact that MDPs generally synergise with lipopolysaccharides (LPS) to cause inflammation and mortality, certain muramyl peptide compounds are actually capable of antagonizing endotoxin activity in vitro and in vivo. Therefore, in spite of the teaching in the art referred to above, some but not all muramyl peptide compounds are useful in the treatment, prophylaxis or management of septic shock and other life-threatening inflammatory conditions mediated by endotoxins such as LPS; and, further, the muramyl peptide compounds useful in the invention can readily be identified on the basis of routine tests not involving undue experimentation.

It has long been known that non-specific stimulation of the immune system can be brought about by exposure to bacteria, or components extracted from bacterial cells. The specific components responsible for this activity were identified as sugar-containing peptides of the cell wall, and further biochemical analysis of the peptides identified them as the peptidoglycan component of the cell wall. The smallest effective synthetic molecule was found to be an N-acetyl-muramyl-L-alanyl-D-isoglutamine (Merser et al, *Biochem. Biophys. Res. Comm.* 66 1316 (1975)). The ability of this compound (now frequently referred to as "prototype muramyl dipeptide" or "prototype MDP") to protect mice against bacterial infection (*Klebsiella pneumonia*) has been described (Chedid et al, *Proc. Natl. Acad. Sci. USA,* 74 2089 (1977)).

Subsequently, a wide variety of analogues of prototype muramyl dipeptide were synthesised, some of which have been proposed as treatments for the restoration of immune function or the non-specific stimulation of the immune system. These analogues, and prototype MDP itself, are muramyl peptide compounds.

According to a first aspect of the present invention, there is provided the use of a muramyl peptide compound which:

(a) is non-pyrogenic or of low pyrogenicity; and/or (b) ameliorates endotoxin-induced weight loss and/or hypophagia; and/or (c) reduces TNF production; and/or (d) stimulates macrophages to process endotoxin;

in the manufacture of a medicament for the treatment or prevention of inflammatory conditions mediated by endotoxin.

The endotoxin will usually be LPS, although the invention also extends to conditions mediated by other endotoxins, for example viral or fungal endotoxins.

Significantly, the muramyl peptides useful in the invention can even be used for the treatment of patients after the onset of septicaemia. In the light of the known properties of prototype MDP, this finding would certainly not have been expected.

A particularly important inflammatory condition which may be treated or prevented by the use of the MDPs is septic shock.

The expression "a muramyl peptide compound" has a clear meaning to those skilled in the art. In particular, it refers to a compound containing one or more sugar residues, at least one of the sugar residues, which will often be a muramic acid residue, being substituted with at least one or more (and usually two or more) amino acid residues. Muramyl peptide compounds may be peptidoglycans which are capable of enhancing the cellular antigenicity response in mammals and which are prototype muramyl dipeptide (MDP) or analogues or derivatives thereof.

The expression "non pyrogenic or of low pyrogenicity" refers to a compound which induces an increase in temperature of an adult human of less than half a degree following the administration of 1 to 2 mg of the compound.

It was suggested in U.S. Pat. No. 4,357,322 that certain muramyl dipeptides may be useful in the treatment of inflammation. However, the range of inflammatory conditions is vast, ranging from the inflammation which occurs after a slight wound to autoimmune disease, bacterial, fungal and viral infections and cancer.

Exactly which inflammatory conditions could be effectively treated using the compounds is not clear from U.S. Pat. No. 4,357,333 and there is certainly no reference to LPS mediated inflammatory conditions. Moreover, the preferred compounds selected in this prior art document are muramyl dipeptide, desmethyl muramyl dipeptide and derivatives of these and it has since been demonstrated that, contrary to the teaching of this prior art document, some of these compounds, do not alleviate LPS mediated inflammation, but, in fact, actually exacerbate it (Parant et al, *Journal of Leukocyte Biology*, 47, 164– 169 (1990)).

Muramyl peptide compounds useful in the invention can be identified by certain of their properties, as briefly stated above. These properties, which may in fact have some common causal link, can be determined as follows.

First, muramyl peptide compounds useful in the invention may be non-pyrogenic. Pyrogenicity may be simply measured by methods well known in the art. If a candidate muramyl peptide compound does not give rise to a statistically and physiologically significant increase in body temperature of a patient and/or an experimental animal, it may be regarded as sufficiently non-pyrogenic to be useful in this invention. Prototype MDP is too pyrogenic to be useful in the invention and so fails at this test.

Secondly, muramyl peptide compounds useful in the invention may have the ability to ameliorate lipopolysaccharide-(LPS-)induced weight loss and/or hypophagia, particularly when administered prior to LPS administration.

During the course of sepsis and in particular septicaemia and septic shock, a rapid loss of body weight is observed. This weight loss effect can also be demonstrated by treating animals with endotoxin such as LPS. Treatment of animals with particular muramyl peptide compounds results in exacerbation of the weight loss-inducing effects of LPS whereas other MDPs muramyl peptide compounds, useful in this invention, protect against weight loss. This protective effect against one of the physiological sequelae of LPS permits the rapid identification of muramyl peptide compounds which may be useful clinically in septic shock and conditions where the effects of LPS are physiologically significant. Muramyl peptide compounds generally have both pyrogenic and weight loss inducing effects. Prototype muramyl dipeptide (MDP) itself exacerbates LPS activity and consequently results in enhancement of weight loss in animals (Langhans et al, *Am. J. Physiol.* 261 R659 (1991)). The induction of weight loss is believed to be in part due to the hypophagic effects of such compounds (ie reduce food intake). Both prototype MDP and LPS are hypophagic. Thus it would be expected muramyl peptide compounds would not be appropriate in the treatment of conditions where LPS is released into the circulation (eg sepsis). As a consequence of this observation and their related pyrogenicity, muramyl peptide compounds have not found a place in the treatment of sepsis. Here it is shown that certain analogues of MDP have an effect which is contrary to that expected; ie, they ameliorate the effects of LPS, unlike prototype MDP (Langhans et al 1991). Further, this observation forms a suitable basis for determining which muramyl peptide compounds are useful in the invention. The following experimental protocol may be followed.

Rats of the Wistar-Porton strain weighing 80–100g are randomized into four groups each containing 6 rats. Animals are caged singly in normal animal house conditions and fed ad libitum standard R&M pellets. Group 1 animals are treated with the muramyl peptide compound under test at a suitable dose (such as 150 µg/kg/day) for an appropriate length of time (for example 7 days). Group 2 animals are treated with the compound under test as for group 1 (eg 150 µg/kg/day for 7 days) and given lipopolysaccharide (LPS) at a suitable dose (such as 3 mg/kg) for an appropriate time period (for example on days 6 and 7). Group 3 animals are treated with saline. Group 4 animals are treated with saline as for group 3 and also with LPS as for group 2. The weights of the animals is monitored.

Figure 8:
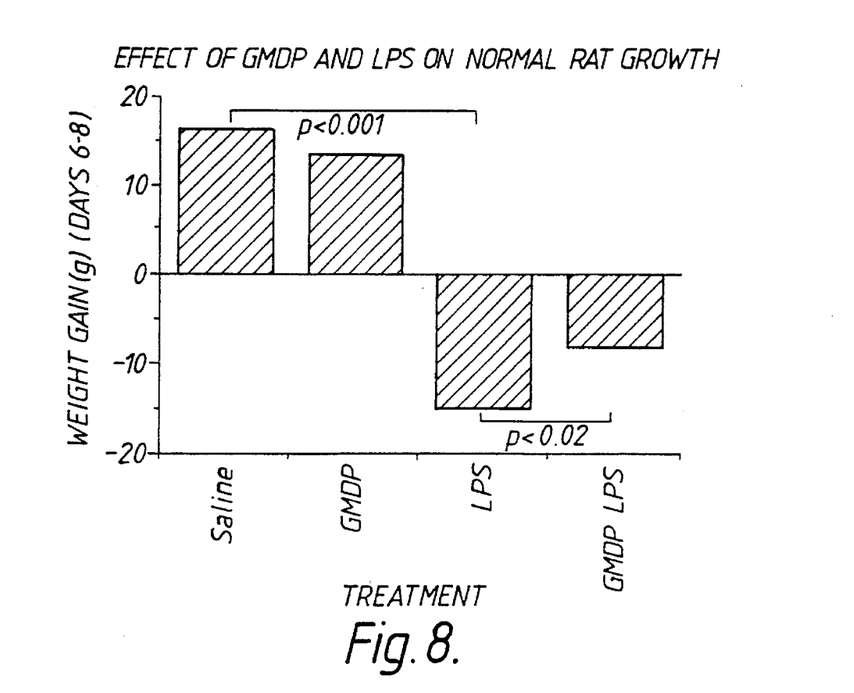
FIG. 8 shows the effect of muramyl peptides on weight loss induced by LPS.

Compounds useful in the invention are those which, at an appropriate dose, result in a statistically significant amelioration of an LPS-induced weight loss. For example, when glucosaminyl muramyl dipeptide (GMDP), a compound useful in the invention as will be explained below, is subjected to the above test, the weight loss results are as shown in FIG. 8, which shows the final weight of the animals in each of groups 1 to 4; a statistically significant amelioration is observed ($P<0.032$ for a comparison of groups 2 and 4; $P<0.001$ for a comparison of groups 3 and 4).

Figure 7:
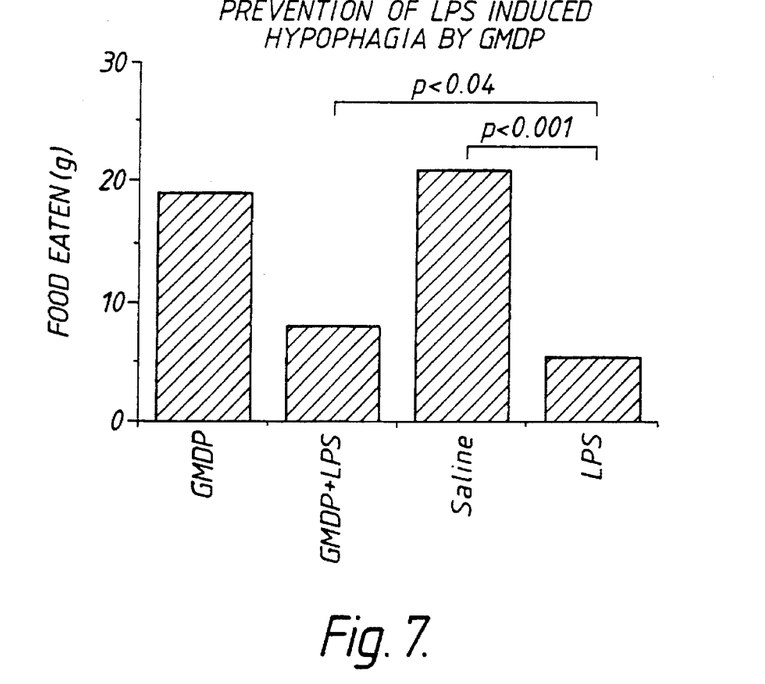
FIG. 7 shows the effect of muramyl peptides on weight loss induced by LPS.

Compounds useful in the invention may also be those which, at an appropriate dose, result in a statistically significant amelioration of LPS-induced hypophagia. For example, when GMDP is subjected to the above test, the hypophagia results are as shown in FIG. 7, which shows the food eaten in each of groups 1 to 4; a statistically significant amelioration is observed ($P<0.04$ for a comparison of groups 2 and 4; $P<0.001$ for a comparison of groups 3 and 4).

Thirdly, muramyl peptide compounds useful in the invention may have the ability to prevent or reduce, to a statistically and physiologically significant degree, the production of tumour necrosis factor (TNF) in patients or animals treated with LPS. A simple screen for useful compounds can be set up on this basis.

Fourthly, muramyl peptide compounds useful in the invention may have the ability to stimulate, to a statistically and physiologically significant degree, macrophages to process LPS. Again, a simple screen for useful compounds can be set up on this basis. Many muramyl peptide compounds useful in this invention fall within general formula I:

wherein:
$R^1$ represents a hydrogen atom or a $C_1$-$C_{22}$ acyl group;
$R^2$ represents a hydrogen atom or a $C_1$-$C_{22}$ acyl group;
$R^3$ represents a hydrogen atom or a $C_1$-$C_6$ alkyl group;
$R^4$ represents a $C_1$-$C_{21}$ alkyl group or a $C_6$ or $C_{10}$ aryl group;
$R^5$ represents a hydrogen atom; and
R represents the residue of an amino acid or a linear peptide built up of from 2 to 6 amino acid residues, at least one of the residues being optionally substituted with a lipophilic group;
other than prototype muramyl dipeptide and desmethylmuramyl dipeptide.

Preferred acyl groups for $R^1$ and $R^2$ are $C_1$-$C_5$ acyl groups such as acetyl; it will be appreciated that the carbon count in the acyl group does not include the carbonyl moiety. Preferred alkyl groups for $R^3$ are $C_1$-$C_4$ alkyl groups such as methyl and ethyl. Preferred alkyl groups for $R^4$ and $C_1$-$C_6$ alkyl groups, particularly $C_1$-$C_4$ alkyl groups, such as methyl or ethyl; phenyl is a preferred aryl group.

R preferably represents a mono-, di- or tri-peptide. The proximal peptide residue (or the only peptide residue, if there is only one) is preferably that of an L-amino acid. Examples include:

| | |
|---|---|
| L-alanyl | L-tryptophanyl |
| L-valyl | L-lysyl |
| L-leucyl | L-ornithyl |
| L-isoleucyl | L-arginyl |
| L-α-aminobutyryl | L-histidyl |
| L-seryl | L-glutamyl |
| L-threonyl | L-glutaminyl |
| L-methionyl | L-aspartyl |
| L-cysteinyl | L-asparaginyl |
| L-phenylalanyl | L-prolyl |
| L-tyrosyl | L-hydroxyprolyl |

L-alanyl is preferred, as is L-threonyl.

The next amino acid from the proximal end of the peptide is preferably of the D-configuration. It is preferably acidic and may be D-glutamic or D-aspartic acid or a mono-, di- or mixed $C_1$-$C_{22}$ (preferably $C_1$-$C_6$) alkyl ester, amide or $C_1$-$C_4$ alkyl amide thereof. (The expression "mixed" is illustrated when one carboxyl group is amidated and the other esterified. D-isoglutamine and D-glutamate are preferred.

A third amino acid residue from the proximal end of the chain, if there is one, is preferably of the L-configuration, as indicated above in relation to the proximal amino acid residue. L-alanyl and L-lysyl are preferred.

The amino acid residue or linear peptide is optionally substituted with at least one lipophilic group. The lipophilic group may be a $C_{10}$-$C_{22}$ acyl group such as stearoyl or a di-($C_{10}$-$C_{22}$ acyl)-sn-glycero-3'-hydroxyphospheryloxy-group wherein for example each of the $C_{10}$-$C_{22}$ acyl groups can be a palmitoyl group. The lipophilic group may alternatively (or in addition, as more than one substitution may be present) be a $C_1$-$C_{10}$ ester group, such as a $C_2$-$C_6$ ester group: a butyl ester is an example.

Examples of muramyl dipeptides within the scope of general formula I include:

muroctasin, otherwise known as MDP-Lys (L18) ($N^2$-(N-acetylmuramyl-L-alanyl-D-isoglutaminyl)-$N^6$-stearoyl-L-lysine);

MTP-PE (N-acetyl-muramyl-L-alanyl-D-isoglutaminyl-L-alanyl- 2-(1',2'-dipalmitoyl-sn-glycero-3'-hydroxyphosphoryloxy)ethylamide, monosodium);

murabutide (N-acetylmuramyl-L-alanyl-D-glutamine-α-N-butyl ester); and t-MDP (N-acetylmuramyl-L-threonyl-D-isoglutamine).

The preparation of muroctasin is disclosed in EP-A-0021367 and U.S. Pat. No. 4,317,771. The preparation of MTP-PE is disclosed in EP-A-0025495. The preparation of murabutide is described in Lefrancier et al, *J. Med. Chem.*, 25 87 (1982). The preparation of t-MDP can be prepared by methods known in the art. Patent publications which give details of the preparations of muramyl peptide compounds generally include BE-A-0834753, BE-A-0834754, BE-A-0847103, BE-A-0849214, DE-A-2710455, DE-A-2922533, DE-A-2747379, DE-A-2912865, FR-A-2355505, FR-A-2358159, FR-A-2375249, EP-A-0004512, EP-A-0002677, JP-A-54063016, JP-A-54073729, JP-A-55019236, U.S. Pat. No. 4,082,735 and U.S. Pat. No. 4,082,736. (The preparation of prototype muramyl dipeptide is disclosed in DE-A-2450355 and U.S. Pat. No. 4,235,771.) All the documents referred to in this specification are incorporated herein by reference.

Not all muramyl dipeptides useful in the present invention fall within general formula I. Many fall within general formula II, which represents a very much preferred group of compounds for use in the invention:

wherein:
R represents a residue of an amino acid or a linear peptide built of from 2 to 6 amino acid residues, at least one of the residues being optionally substituted with a lipophilic group; and
n is 1 or 2.

Preferred values for R are as described above in relation to general formula I. It is particularly preferred that the peptide R correspond to the peptide in prototype MDP (L-Ala-D-isoGln). Alternatively, in another preferred embodiment, R may represent L-Ala-D-Glu.

The preferred value for n is 1.

Compounds of general formula II are disclosed in U.S. Pat. No. 4,395,399 and the preferences set out in that document are equally preferred in the present invention. Additionally, in this invention, the group R may be substituted lipophilically as described above.

One of the most preferred compounds for use in the present invention falls within general formula II and is N-acetyl-D-glucosaminyl-(β1–4)-N-acetylmuramyl-L-alanyl-D-isoglutamine (GMDP), the structure of which is:

GMDP

This compound (Compound II in U.S. Pat. No. 4,395,399), also known as glycopin, has already undergone pre-clinical toxicity testing and pharmacokinetic investigations required for licensing for clinical use in the USSR (as it then was). The acute toxicity in mice, measured by the $LD_{50}$ test is 7 g/kg. This figure shows the compound to be almost an order of magnitude less toxic than muroctasin which has an $LD_{50}$ value in mice of 625 mg/kg.

While the pyrogenicity of GMDP is sufficiently low to make it suitable for use in the present invention, and not to have prevented its-clinical evaluation for other purposes, it may in some circumstances be preferable to use an even less pyrogenic analogue. Such an analogue is available, and is N-acetyl-D-glucosaminyl-(β1–4)-N-acetylmuramyl-L-alanyl-D-glutamic acid (GMDP-A), which is Compound III in U.S. Pat. No. 4,395,399, and whose structure is as follows:

GMDP-A

Other preferred compounds within the scope of general formula II include:

N-acetyl-D-glucosaminyl-(β1–4)-N acetylmuramyl-L-alanyl-L-isoglutamine (GMDP-LL) which has the structure:

GMDP-LL

N-acetyl-D-glucosaminyl-(β1–4)-N acetylmuramyl-L-alanyl-D-glutamine n-butyl ester (GMDP-OBu) which has the structure:

GMDP-OBu

N-acetyl-D-glucosaminyl-(β1–4)-N acetylmuramyl-L-alanyl-D-isoglutaminyl-L-lysine (GMDP-Lys) which has the structure:

GMDP-Lys

N*-[N-acetyl-D-glucosaminyl-(β1–4)-N-acetylmuramyl-L-alanyl-D-isoglutaminyl] -N*-stearoyl-L-lysine (GMDP-Lys(St)) which has the structure:

GMDP-Lys(St)

Other useful compounds include:

N\*-[N-Acetyl-D-glucosaminyl-(β1–4)-N-acetyl-muramyl-L-alanyl-γ-D-glutamyl]-N\*-stearoyl-L-lysine which has the structure:

GMDPA-Lys(St)

N-Acetyl-D-glucosaminyl-(β1–4)-N-acetylmuramyl-L-alanyl-D-glutamic acid dibenzyl ester which has the structure:

GMDPA(OBzl)$_2$

N-Acetyl-D-glucosaminyl-(β1–4)-N-acetylmuramyl-N-methyl-L-alanyl-D-isoglutamine which as the structure:

Me-GMDP

N-Acetyl-D-glucosaminyl- (β1–4)-N-acetylmuramyl-(β1–4)-N-acetyl-D-glucosaminyl-(β1–4)-N-acetylmuramyl-bis-(L-alanyl-D-isoglutamine) which has the structure:

(GMDP)$_2$

N-Acetyl-D-glucosaminyl-(β1–4)-N-acetylmuramyl-(β1–4)-N-acetyl-D-glucosaminyl-(β1–4)-N-acetylmuramyl-bis-(L-alanyl-D-glutamic acid) which has the structure:

(GMDPA)₂

N-Acetyl-D-glucosaminyl-(β1–4)-N-acetylmuramyl-(β1–4)-N-acetyl-D-glucosaminyl-(β 1–4)-N-acetylmuramyl-bis-(L-alanyl-D-isoglutaminyl-L-lysine) which has the structure:

(GMDP Lys)₂

N-acetyl-D-glucosaminyl-(β1–4)-N-acetylmuramyl-(β1–4)-N-acetyl-D-glucosaminyl-(β1–4)-N-acetylmuramyl-bis-[L alanyl-D-isoglutaminyl-N*-stearoyl-L-lysine]:

[GMDP-Lys(St)]₂

N-Acetyl-D-glucosaminyl-(β1–4)-N-acetylmuramyl-L alanyl-D-isoglutamine 1-adamantyl ester which has the structure:

GMDP-Ad

L-Threonyl-N*-[N-Acetyl-D-glucosaminyl-(β1–4)-N-acetylmuramyl-L-alanyl-γ-D-isoglutaminyl]-L-lysyl-L-prolyl-L-arginine which has the structure:

GMDP-tuftsin E

N-Acetyl-D-glucosaminyl-(β1–4)-N-acetyl-muramyl-L-alanyl-γ-D-isoglutaminyl-L-threonyl-L-lysyl-L-prolyl-L-arginine which has the structure:

GMDP-tuftsin A

N-Acetyl-D-glucosaminyl-(β1–4)-N-acetylmuramyl-L-alanyl-α-D-glutamyl-L-lysyl-L-threonyl-N*-stearoyl-L-lysyl-L-prolyl-L-arginine which has the structure:

GMDPA-tuftsin lipophilic

N*-[N-Acetyl-D-glucosaminyl-(β1–4)-N-acetyl-muramyl-L-alanyl-γ -D-isoglutaminyl]-L-lysyl-L-histidyl-L-glycine amide which has the structure:

N-Acetyl-D-glucosaminyl-(β1–4)-N-acetylmuramyl-L-alanyl-D-isoglutaminyl-L-glutamyl-L-tryptophan which has the structure:

GMDP-thymogen I

N-Acetyl-D-glucosaminyl-(β1–4)-N-acetylmuramyl-L-alanyl-D-isoglutaminyl-ε-aminohexanoyl-L-glutamyl-L-tryptophan which has the structure:

N*-[N-Acetyl-D-glucosaminyl-(β1–4)-N-acetyl-muramyl-L-alanyl-D-isoglutaminyl] -N*-stearoyl-L-lysyl-L-glutamyl-L-tryptophan which has the structure:

GMDPA-bursin

N-acetylmuramyl-L-threonyl-D-isoglutamine which has the structure:

Thr-MDP

GMDP-thymogen II

GMDP-thymogen III

N-acetylmuramyl-L-alanyl-D-glutamine n-butyl ester which has the structure:

Murabutide

In the above structures, the following abbreviations are used:

Bzl - benzyl;

Me - methyl;

Ahx - ε-aminohexanoyl.

The most preferred compound is GMDP followed by GMDP-A, and murabutide.

Glucosaminyl-muramyl dipeptides within the scope of general formula II can be prepared relatively cheaply and in reasonably large quantities by the process disclosed in U.S. Pat. No. 4,395,399. The preparation disclosed is based on the extraction and purification of the disaccharide component from the bacterium *Micrococcus lysodecticus* and its subsequent chemical linkage to a dipeptide synthesised for example by conventional peptide chemistry. However, the disaccharide may equally well be chemically synthesised using standard sugar chemistry.

As previously stated, by means of the present invention, muramyl dipeptides are useful in the treatment or prevention of septic shock and/or other life-threatening inflammatory conditions mediated by LPS and including cachexia. The invention has particular application in treating, preventing or managing complications arising from bacterial infection after surgery, particularly in the case of abdominal operations because of the possibility of gut flora invading the peritoneal cavity. However, there is also a risk of infection after other types of surgery such as thoracic surgery and surgery for the treatment or removal of the gall bladder. In addition, bacterial sepsis and ultimately septic shock may arise from a chronic or acute bacterial infection of an organ, such as the lung or the urinogenital system, from pneumonia, from a perforated ulcer, from pancreonecrosis or from inflammation of the gall bladder.

Conditions to which the invention has application therefore include pneumonia, surgical wound infection, suppuration of the small pelvis, peritonitis, peritoneal abscess, paracolostomic abscess, cholangitis, empyema of the gall bladder, phlegmon of front abdomen, phlegmon of the sigma and postinjective abscess, as well as to the related complications of endotoxaemia, glucose depression, hypotension, cardiac arythmia and vasodilation. A condition to which the invention has particular application is in surgery in immunosuppressed individuals. This is because such patients are especially likely to develop infections and to have low lymphocyte and neutrophil counts. The muramyl dipeptides useful in the present invention may be of added benefit to these patients because of their immunorestorative actions on neutrophils and lymphocytes as well as their protective effects against endotoxins. Immunosuppressed patients include cancer patients, since the presence of a tumour is likely to lead to suppression of the immune system. Furthermore, both chemotherapy and radiation therapy also have the side effects of immunosuppression.

From the above, it can be seen that the invention also relates to a method for the treatment, prevention or management of septic shock and/or other life-threatening inflammatory conditions mediated by endotoxins such as LPS, the method comprising administering to a patient an effective amount of a muramyl dipeptide. Preferences for this aspect of the invention are as given above.

As briefly discussed previously, muramyl peptide compounds useful in the invention may be administered either parenterally or non-parenterally. The most usual and, indeed, the preferred route of administration is oral administration but other non-parenteral routes include nasal or buccal administration or administration by inhalation. Formulations for parenteral administration will generally be sterile. One or more suitable carriers will be present, such as physiological saline. Muramyl peptide compounds may be lyophilised with a protectant compound such as glycine prior to formulating with physiological saline or water for injection.

A muramyl peptide compound useful in the invention may be the sole active ingredient in a pharmaceutical composition. It may be preferred, though, for other active ingredients to be present as well. For example, antibiotics or other antibacterials may usefully be present when the life-threatening inflammatory condition has a bacterial aetiology; other microbially or virally mediated inflammatory conditions would be treated with other antimicrobials or antivirals; and cancers would be treated by anticancer agents such as vinblastin, adriomycin, actinomycin D, methotrexate and mitomycin C.

Oral formulations are preferred, particularly those in the form of tablets. One or more suitable carriers may be present. Typical carriers include lactose, saccharose, potato starch, calcium stearate and methyl cellulose.

The precise dosage for administration will always be that deemed suitable by the clinician or physician. Subject to that, a daily dosage in the range of from 0.1 to 100 mg per day (or per tablet or other unit dose) may be found to be acceptable, with a range of 0.5 mg to 5 mg or 10 mg per day (or per tablet or other unit oral dose) being preferred. A daily dosage of 1 to 2 mg is considered to be optimal.

Dosages for parenteral (for example, intravenous, intramuscular or subcutaneous) administration will generally be lower, with from 0.01 mg to 1 mg per day (or per unit dose) being suitable. A range of from 0.05 mg to 0.5 mg per day (or per unit does) is preferred, and a dosage of about 0.1 mg per day is optimal.

The timing of the dosage will also be best determined by the clinician or physician. In the case of prophylaxis of septic shock and other inflammatory conditions likely to result from surgery, there may be advantages in administering the formulations before surgery.

In addition, the compounds may also be used in patients not undergoing surgery, to reduce septic complications and mortality.

The invention will now be illustrated by the following non-limiting examples and the drawings in which.

EXAMPLE 1

Use of the N-acetyl-glucosaminyl-N-acetyl-muramyl-L-alanyl-D-isoglutamine (GMDP) to prevent post-operative complications due to bacterial infections, to maintain neutrophil function and ultimately to reduce mortality in patients undergoing surgery for colon cancer.

All the patients entering this trial were about to undergo major abdominal surgery for the resection of carcinoma of the colon.

Prior to the operation (day −3) the neutrophil function of all patients was monitored by a series of tests.

Neutrophils were isolated from peripheral blood. 3.5 ml of heparinised blood was spread over M-PRM medium (Flow Laboratories) and centrifuged for 40 minutes at 400g at 20° C. The lower interphase containing up to 97% of neutrophils was removed, and the cells were washed three times with Hank's balanced salt solution. Leucocyte viability (trypan blue) was not less than 98%. The cells were adjusted to a concentration of $2 \times 10^6$ ml.

The following parameters were measured:

- Adhesion: 100 μl of neutrophil suspension were placed in the wells of a flat-bottomed culture dish, and incubated at 37° C. for 60 minutes. After washing off the non-adhesive cells, the adhered neutrophils were fixed with ethanol and stained with Romanovsky-Giemsa dye. After washing out the free dye, the cell-associated dye was dissolved in isopropanol, and the optical density ($OD_{650}$) of the solution was determined using an "ELISA II" microprocessor (Boehringer). The number of adherent cells was calculated by reference to a standard curve.

- Chemiluminescence: Luminol-dependent chemiluminescence was measured on a 1251 Luminometer (LKB).

- Superoxide anion production was determined by the NBT test (Merck).

- Myeloperoxidase: 100 μl of substrate mixture, consisting of 0.04% orthophenylene diamine (Sigma) and 0.014% hydrogen peroxide in phosphate citrate buffer (pH 5.0) was added to cells and incubated for 10 minutes before the reaction was stopped with 100 μl of 10% sulphuric acid. The optical density at 492 mu was measured with a Multiscan Titertek Plus (Flow Laboratories).

- Acid phosphatase: 50 μl of substrate mixture, consisting of 0.24% paranitrophenyl phosphate (Boehring) and 0.84% NaCl in a sodium citrate buffer (pH 5.5) were added to cells and incubated for 30 minutes at 30° C. before the reaction was by adding 100 μl of 0.2M NaOH. The optical density at 405 mu was measured with a Multiscan Titertek Plus (Flow Laboratories).

For chemiluminescence, superoxide anion production, myeloperoxidase and acid phosphatase both the spontaneous and induced reactions were measured. Induction was performed by exposing the cells to opsonized zymosan (30 μl, 20 mg/ml) for 30 minutes at 37° C. before the assay.

In the treated group GMDP was given per os on days −2 and −1 before the operation, and subcutaneously on days +1, +2 and +3 after the operation at a dose of 1–2 mg/day. The total dose of GMDP was 3–7 mg. On day +5 after the operation neutrophil function was again assessed in all patients by the same parameters as specified above.

The patients were monitored for post-operative sepsis for four weeks following the operation. The septic complications which were scored included disseminated sepsis, pneumonia, peritonitis and abdominal abscesses, all of which are known to lead to septic shock. The results are presented in Tables 1 and 2.

TABLE 1

Effect of treatment with GMDP before and after the operation on the incidence of septic complications following resection of carcinoma of the colon.

| | Total No of Patients | No of Patients with Septic Complications | Incidence of Septic Complications (%) | Mortality (%) |
|---|---|---|---|---|
| Control | 20 | 10 | 50 | 15 |
| GMDP-treated | 16 | 3 | 18.75 | 6.25 |

From Table 1 it may be seen that GMDP treatment reduced the incidence of septic complications from 50% to 18.75%. Importantly and more specifically, the reduction in mortality from 15% to 6.25% gives an indication of the effectiveness of the invention in treating or preventing septic shock, which is frequently the cause of death in such mortalities.

TABLE 2

Neutrophil function in control and GMDP-treated patients undergoing resection of carcinoma of the colon.

| | Control | | | GMDP-treated | | |
|---|---|---|---|---|---|---|
| | Day −3 | Day +5 | % Change | Day −3 | Day +5 | % Change |
| Adhesion (O.D. 650μ) | 54.3 ± 4.6 | 33.8 ± 5.4 | −37.8 | 39.8 ± 5.4 | 47.9 ± 12.6 | +20.4 |
| Chemilumeniscence (mV) | | | | | | |
| Spontaneous | 2.3 ± 0.31 | 1.39 ± 0.2 | +6.9 | 1.82 ± 0.07 | 3.37 ± 0.70 | +85.2 |
| Induced | 19.2 ± 2.4 | 11.8 ± 2.3 | −38.5 | 11.3 ± 2.1 | 15.8 ± 4.2 | +39.8 |
| Superoxide | | | | | | |
| Spontaneous | 110.2 ± 10.1 | 63.9 ± 8.5 | −42.0 | 78.9 ± 15.7 | 97.6 ± 12.8 | +23.7 |
| Induced | 148.1 ± 19.2 | 119.2 ± 10.6 | −19.5 | 133.7 ± 16.1 | 134.9 ± 11.3 | +0.9 |
| Myeloperoxidase (O.D. 492μ) | | | | | | |
| Spontaneous | 1149.3 ± 150 | 993.2 ± 178 | −13.6 | 1145 ± 204.1 | 1075 ± 178.3 | −6.1 |
| Induced | 811.3 ± 99.3 | 894.1 ± 158 | +10.2 | 948.3 ± 205 | 948.3 ± 205 | +11.2 |

TABLE 2-continued

Neutrophil function in control and GMDP-treated patients undergoing resection of carcinoma of the colon.

|  | Control | | | GMDP-treated | | |
|---|---|---|---|---|---|---|
|  | Day −3 | Day +5 | % Change | Day −3 | Day +5 | % Change |
| Acid Phosphatase (O.D. 405μ) | | | | | | |
| Spontaneous | 178.3 ± 48.1 | 114.7 ± 7. | −35.7 | 133.8 ± 75 | 114.9 ± 2.4 | −14.1 |
| Induced | 138.9 ± 21.6 | 110.8 ± 11.5 | −20.2 | 172.3 ± 18.8 | 120.8 ± 3.2 | −29.94 |

From Table 2 it may be noted that, without GMDP treatment, there was a reduction in most of the parameters of neutrophil function following the operation. In the case of adhesion, chemiluminescence and superoxide production GMDP treatment prevented this reduction and instead caused an increase in neutrophil function. This was not observed for myeloperoxidase and acid phosphatase.

EXAMPLE 2

Use of N-acetyl-glucosaminyl-N-acetyl-muramyl-L-alanyl-D-isoglutamine (GMDP) to arrest the progression of acute sepsis, and to maintain neutrophil function in patients suffering from acute sepsis.

The patients entering this trial were already suffering from serious systemic bacterial sepsis arising as a result of destructive cholecystitis, abscesses of the abdominal cavity, peritonitis, pancreonecrosis and post-operative pneumonia.

On day before treatment with GMDP (day −1) the neutrophil function of all patients was measured by the tests described above in Example 1. In the GMDP-treated group, GMDP was administered parenterally at a dose of 1–2 mg/day for five consecutive days. The total dose of GMDP was 5–7 mg.

One day after the cessation of GMDP treatment (day +6), neutrophil function was again measured in all patients. The results are presented in Table 3 and 4.

shows the effectiveness of the invention.

TABLE 3

Effect of GMDP on progression of sepsis in patients sufferent septic complication.

|  | Total No Patients | No of patients with progression of septic complications | Incidence of progression of septic complications (%) | Mortality (%) |
|---|---|---|---|---|
| Control | 18 | 11 | 61 | 27 |
| CMDP-treated | 14 | 4 | 28.6 | 14.3 |

From Table 3 it may be seen that GMDP treatment reduced the incidence of the progression of septic complications from 61% to 28.6%. Again, importantly and more specifically, the reduction in mortality from 27% to 14.3%

TABLE 4

Neutrophil function in patients suffering from sepsis without or with GMDP treatment.

|  | Control | | | GMDP-treated | | |
|---|---|---|---|---|---|---|
|  | Day −1 | Day −6 | % Change | Day −1 | Day +6 | % Change |
| Adhesion (O.D. 650μ) | 52.3 ± 5.7 | 40.4 ± 8.1 | −22.8 | 34.6 ± 6.2 | 52.3 ± 2.3 | +51.2 |
| Chemiluminescent (mV) | | | | | | |
| Spontaneous | 1.61 + 0.18 | 1.93 ± 0.32 | +19.9 | 2.41 ± 0.14 | 4.16 ± 0.14 | +72.6 |
| Induced | 16.3 ± 3.4 | 13.2 ± 5.6 | −19.0 | 9.41 ± 2.1 | 21.3 ± 3.51 | +126.4 |
| Superoxide (O.D. 540μ) | | | | | | |
| Spontaneous | 101.3 ± 4.2 | 88.4 ± 16.3 | −12.7 | 55.5 ± 6.4 | 84.3 ± 8.7 | +51.9 |
| Induced | 196.4 ± 13.4 | 169.4 ± 13.4 | −13.7 | 92.1 ± 3.21 | 141.1 ± 8,3 | +53.2 |
| Myeloperoxidase (O.D. 492μ) | | | | | | |
| Spontaneous | 893.3 ± 26.2 | 604 ± 96.3 | −32.4 | 504.5 ± 118 | 595.2 ± 48.3 | +17.9 |
| Induced | 697.2 ± 19.4 | 419. ± 19.4 | −39.9 | 520.3 ± 60.1 | 587.1 ± 96.3 | +12.8 |
| Acid phosphatase (O.D. 405μ) | | | | | | |
| Spontaneous | 116.7 ± 16.3 | 129.6 ± 24.4 | +11.1 | 119.4 ± 10.1 | 251.3 ± 16.1 | +110.5 |
| Induced | 169.3 ± 15.1 | 126.6 ± 14.1 | −25.2 | 104.4 + 3.6 | 201 ± 14.3 | +92.5 |

From Table 4 it may be noted that, in the control group who were not treated with GMDP, there was a deterioration in nearly all parameters of neutrophil function between day −1 and day +6, but this was prevented, and reversed into an improvement by GMDP treatment.

This example provides a clear demonstration that GMDP is an effective treatment even after the onset of sepsis. Although prototype MDP has been shown to have antibacterial activity, it would certainly not reduce mortality under the circumstances of this experiment.

EXAMPLE 3

Effects of MDPs on LPS-induced mortality in mice.

Figure 1:
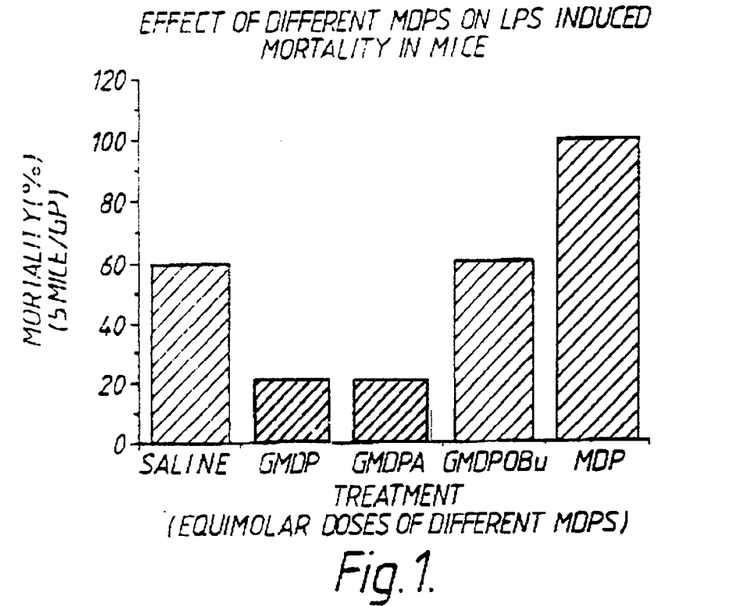
FIG. 1 shows the effects of MDPs on LPS-induced mortality in mice.

25 female BALB/c mice weighing 16–18 g each were divided into 5 groups, each group containing 5 animals. Each group of mice received twice-daily doses of saline, GMDP, GMDP-OBu, MDP or GMDP-A. The compounds were administered by intra-peritoneal injection in twice-daily doses of 100 μg or the molar equivalent per mouse during a 9-day period before the injection of 300 μg LPS per mouse. Mortality was determined 2 days after LPS administration and the results are presented in FIG. 1. FIG. 1 shows that certain types of muramyl peptides, such as prototype MDP, synergise with LPS to cause an increase in mortality over and above that seen in mice receiving saline. In contrast, GMDP and GMDP-A antagonise the effect of LPS. Thus GMDP and GMDP-A would be useful in the treatment and prevention of sepsis and septic shock, whereas MDP and GMDP-OBu would not.

EXAMPLE 4

Effects of muramyl peptides on the phagocytic activity of macrophages.

This experiment attempts to show the effect of various MDPs on phagocytic activity of macrophages; the greater the phagocytic activity, the more effective the MDP in inducing resistance to LPS. Mice were divided into 9 groups and to each group was administered one of the following: saline, MDP, MDP-OBu, MDP-Thr, GMDP, MDP-Lys(St), GMDP-OH and GMDP-LL.

Figure 2:
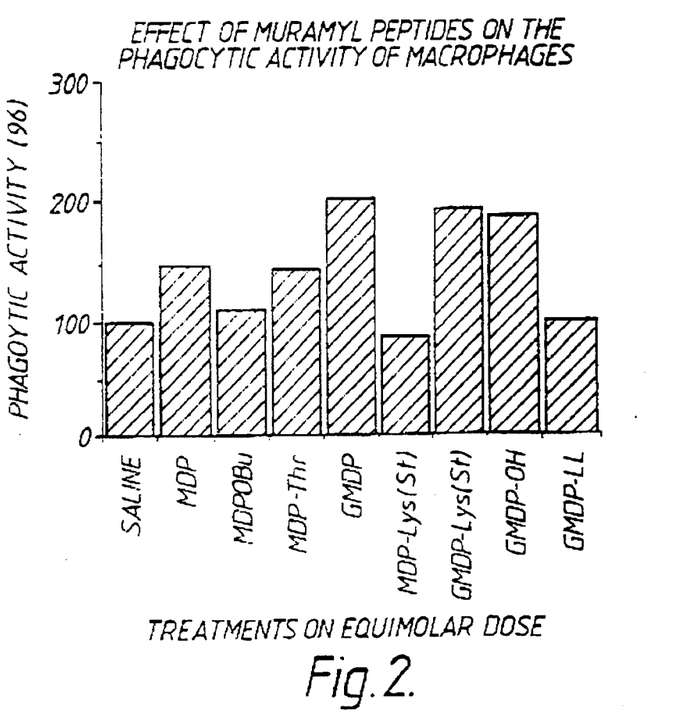
FIG. 2 shows the effects of muramyl peptides on the phagocytic activity of macrophages.

The compound under test was injected into the peritoneal cavity of mice, each mouse receiving 100 μg or an equimolar equivalent dose. Control mice received 200 μl of saline. One day after injection of the muramyl peptide, a lethal does of LPS (300 μg per mouse) in 200 μl of physiological saline was injected intraperitoneally and after 20 minutes, 1 ml of black ink was also administered intraperitoneally. 10 minutes later, peritoneal macrophages were obtained and washed twice. The number of cells was counted and then the macrophages were lysed and the optical density of the supernatant was determined at 610 nm. The results are shown in FIG. 2 which demonstrates that GMDP is potent in increasing macrophage activity and that other MDPs also have this property. It is generally considered that increasing phagocytic activity of macrophages will correlate with the ability of the animal to process bacteria and LPS. Therefore, GMDP, GMDP-Lys(St) and GMDP-OH would be useful in sepsis and septic shock. However, along with the results of this assay, it is also necessary to take into account other activities of MDPs, since some will be more pyrogenic than others.

EXAMPLE 5

Effect of MDPs on TNF production in whole blood culture.

Figure 3:
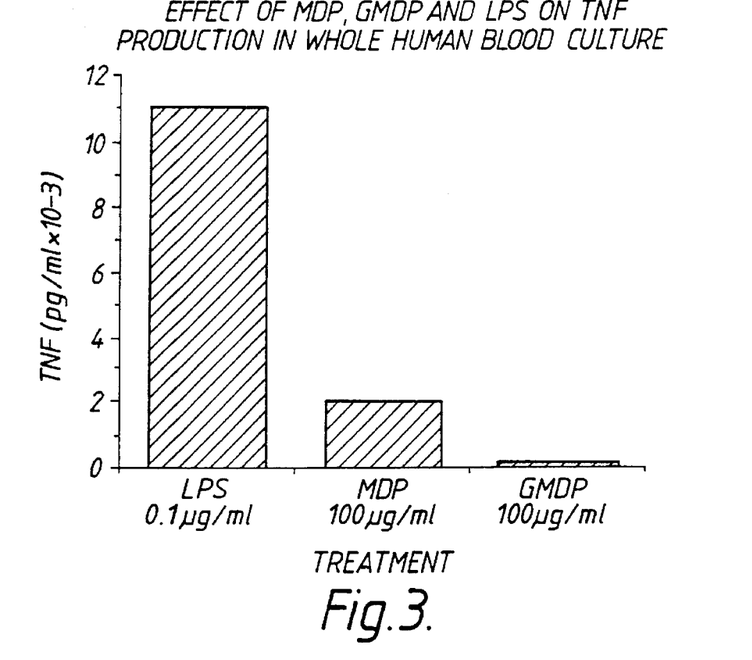
FIG. 3 shows the effects of muramyl peptides on TNF production in whole blood culture.

Whole heparinized human blood was diluted 1:2 with RPMI and dispensed into 96-well microtitre plates. Individual wells were treated with saline, GMDP, MDP or LPS at the doses shown above. After incubating at 37° C. for 6 hours, the supernatants were assayed for TNFα by a standard capture ELISA method. The results are shown in FIG. 3 which indicates that GMDP is a poor inducer of TNF, whereas MDP and LPS both have significant TNF inducing ability. This is a sensitive assay for measuring the effect of mediators on immune cell production of TNFα which is believed to be a primary mediator of inflammation, coagulopathy and death in sepsis and septic shock. It can be seen that GMDP is the least inflammatory mediator; the respective TNF inducing activities of these substances would inadvertently correlate with their toxicities.

EXAMPLE 6

Suppression of IL-1 production by different MDPs.

Mice (BALB/c, female) 13–14 g, 5 animals in each group, received 2 injections of MDPs, 12 hours apart. The MDPs tested were MDP, muroctasin, MDP-Thr, MDP-OBu, GMDP-LL, GMDP-Lys(St) and GMDP-A. After the last injection, peritoneal cells were collected and the induction of IL-1 secretion by peritoneal macrophages was tested.

Preparation of peritoneal macrophages:

Macrophages were collected from the peritoneal cavity of mice by lavage with Hank's balanced salt solution. After washing the cells, they were then placed in wells of flat-bottomed 96-well plates and incubated at 37° C. for 1 hour in RPMI containing 5% FCS. The plates were then washed with warm RPMI to remove non-adhering cells. LPS (25 μg/ml) was then added in fresh culture medium and the plates were further cultured for 24 hours.

Figure 4:
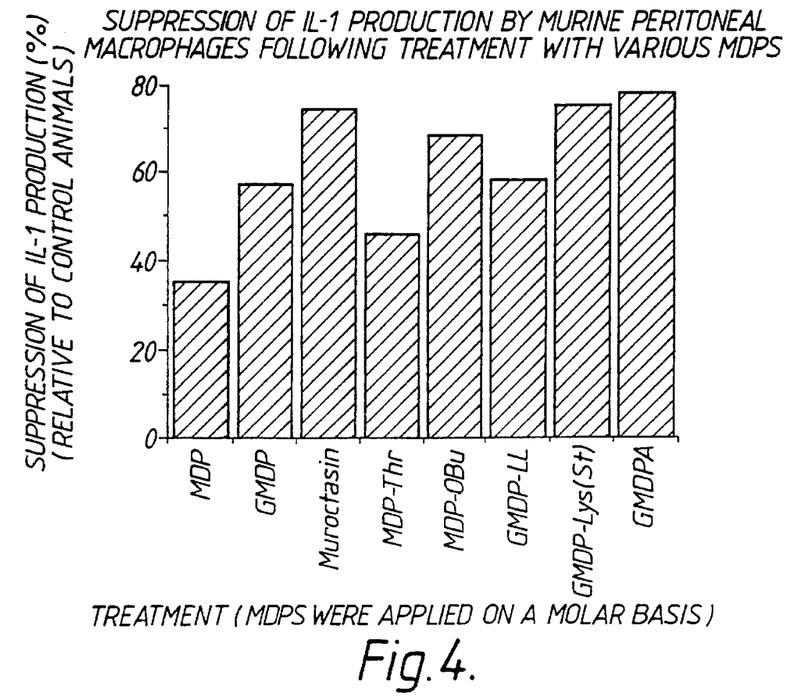
FIG. 4 shows the suppression of IL-1 production by MDPs.

IL-1 production by peritoneal macrophages:

Production of IL-1 by peritoneal macrophages was assayed by thymocyte co-stimulation bioassay. Thymocytes from (CBA*C57BL.6)F1 mice (106), PHA (1 μg.ml), and the tested supernatant (50 μl) were placed into the wells of flat-bottomed 96-well plates. Thymocyte proliferation rate was measured 72 hours later by the incorporation of 3H TdR (1 μCi.well) during 6 hours prior to culture termination. The results are shown in FIG. 4.

In addition to TNFα, IL-1 has been proposed to be a cytokine with a central role in immune response and inflammation. As with TNFα, IL-1 is produced in response to LPS stimulation. FIG. 4 shows that GMDP, muroctasin, MDP-OBu, GMDP-Lys(St) and GMDP-A can all suppress the IL-1 response to LPS. MDP and MDP-Thr are poor in this quality. As with the previous figures, this data must be considered together with the effects of MDPs on TNF, macrophage phagocytic activity and other in vivo models. However, the distinction between MDP and GMDP is again clear.

EXAMPLE 7

Effects of MDP analogues on LPS induction of serum TNF.

In this experiment, 4 compounds were tested and these are: MDP, GMDP-A, GMDP-OBu and GMDP. Saline was administered to control mice. BALB/c mice (6 mice/group) were injected intraperitoneally with 1.4 mg of dead *C. parvum* (0.2 ml of a 7 mg/ml suspension.). Mice were subsequently (2 weeks later) treated with saline, MDP (100 μg) or analogue (100 μg) in 0.5 ml saline IP. The dose of each 'MDP' was adjusted so that animals received equimolar amounts. LPS (25 μg) was injected 18 hours after the injection of MDP/analogue and mice were subsequently sacrificed and bled out. TNF was determined by standard capture ELISA assay.

Figure 5:
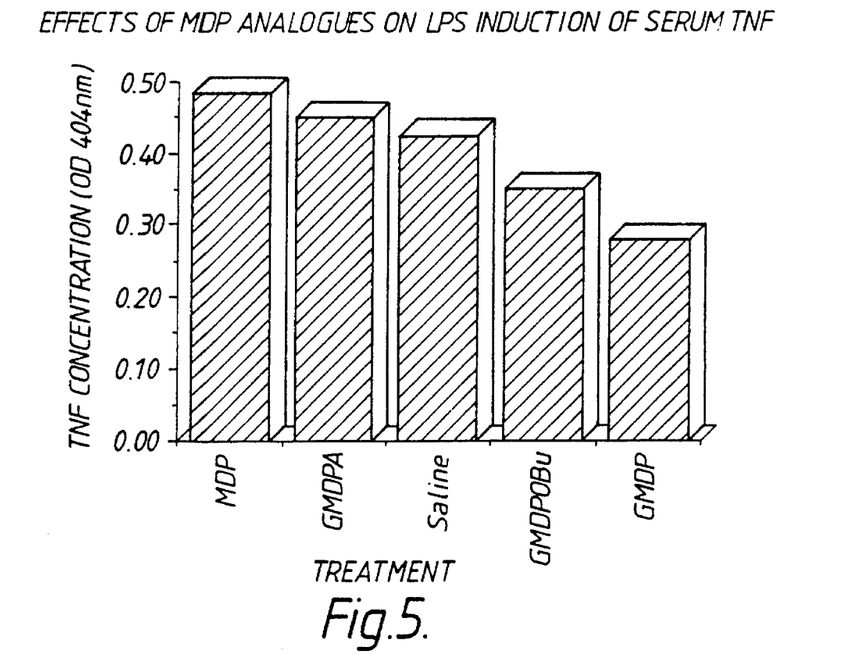
FIG. 5 shows the effects of MDPs on LPS induction of serum TNF.

The results are shown in FIG. 5 which demonstrates that GMDP proved to be able to suppress the production of TNFα, thus showing that it is an anti-inflammatory substance. In contrast, MDP and GMDP-A were pro-inflammatory, causing an enhancement of the TNF levels induced by LPS. Again, as with previous experiments, this data must be considered together with the other properties of MDPs.

EXAMPLE 8

TNF induction by muramyl peptides.

Here, the muramyl peptides tested were prototype MDP, GMDP, GMDP-A, GMDP-OBu, GMDP-Lys(St), GMDPA-Lys(St), GMDP-Benz and Thr-MDP.

BALB/mice (6 mice/groups) were injected intraperitoneally with 1.4 mg of dead *C. parvum* (0.2 ml of a 7 mg/ml suspension). Mice were subsequently (2 weeks later) treated with saline, MDP (100 μg) or analogue (100 μg) in 0.5 ml saline IP. The dose of each 'MDP' was adjusted so that animals received equimolar amounts. LOS (25 μg) was injected 18 hours after the injection of MDP/analogue and the mice were subsequently sacrificed and bled out. TNF was determined by standard capture ELISA assay.

Figure 6:
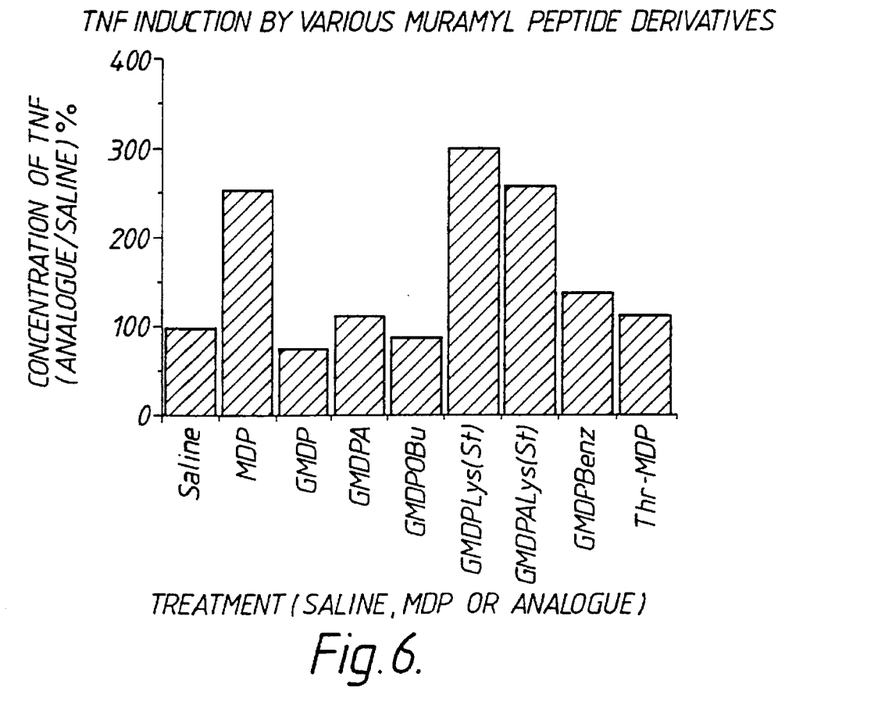
FIG. 6 shows the ability of muramyl peptides to suppress TNFα production.

The results are shown in FIG. 6 which provides further evidence for the ability of GDMP to suppress TNFα production, and this result is consistent with the results of Example 7. GMDP-Lys(St) and GMDPA-Lys(St) also enhance LPS-induced TNF production, but GMDP-OBu has consistently failed to synergise with LPS.

EXAMPLE 9

Prevention of LPS-induced hypophagia and effect on normal rat growth.

In this experiment, results were compared for rats receiving GMDP alone, GMDP plus LPS, saline and LPS.

Rats of the Wistar-Porton strain weighing 80–100 g were randomised into groups, each containing 6 rats. Animals were fed ad libitum (std R&M pellets), caged singly and maintained under normal animal house conditions. Cumulative feed intake was determined on days 7 and 8. GMDP was administered for the 8-day period (150 μg/kg/day); in groups also receiving LPS (3 mg/kg/day), the endotoxin was administered on days 6 and 7. In LPS only treated groups the animals received saline (0.1 ml) for days 1–5 and LPS on days 6 and 7 (3 mg/kg/day). Statistical significance was determined by unpaired student's T test.

LPS can induce rapid weight loss in animals. One of the characteristics of chronic or acute infection is loss of weight, and the weight loss observed can be accounted for catabolism of tissue and reduction of food intake. FIG. 7 shows that GMDP significantly antagonises LPS-induced hypophagia (anorexia) whilst FIG. 8 shows that GMDP antagonises LPS weight loss. This is surprising and in contrast to what is known about MDP which synergises with LPS to result in enhancement of weight loss and reduction in diet consumption.

I claim:

1. A method for treatment of an inflammatory condition mediated by an endotoxin, including septic shock, which comprises administering to a patient an effective amount of a muramyl peptide compound having the following structural formula:

wherein:

R represents L-alanyl-D-isoglutamine (GMDP).

2. The method of claim 1 in which said GMDP is administered in combination with an antibiotic.

3. The method of claim 1 wherein said administration is oral in the amount of 0.1 to 10 mg per day.

4. The method of claim 1 wherein said administration is parenteral in the amount of 0.01 to 1 mg per day.

5. A method for treatment of an inflammatory condition mediated by an endotoxin, including septic shock, which comprises administering to a patient an effective amount of a muramyl peptide compound having the following structural formula:

wherein:

R represents L-alanyl-D-glutamic acid (GMDP-A).

6. The method of claim 5 in which said GMDP-A is administered in combination with an antibiotic.

7. The method of claim 5 wherein said administration is oral in the amount of 0.1 to 10 mg per day.

8. The method of claim 5 wherein said administration is parenteral in the amount of 0.01 to 1 mg per day.

\* \* \* \* \*